United States Patent [19]

Lawlor

[11] Patent Number: 5,203,035
[45] Date of Patent: Apr. 20, 1993

[54] VISION CLEARING DEVICE

[76] Inventor: James F. Lawlor, 4475 Mission Blvd., #233, San Diego, Calif. 92109

[21] Appl. No.: 931,204

[22] Filed: Aug. 17, 1992

[51] Int. Cl.$^5$ .............................................. A61F 9/02
[52] U.S. Cl. .......................................... 2/438; 2/434
[58] Field of Search ................... 2/422, 425, 424, 426, 2/428, 429, 430, 431, 432, 434, 435, 438, 439, 441, 447, 448, 449, 450, 452, 454, 8, 9, 10, 12, 13

[56] References Cited

U.S. PATENT DOCUMENTS

| 857,689 | 6/1907 | Tileston | 2/454 |
| 3,027,562 | 4/1962 | Widenor | 2/430 |
| 4,428,081 | 1/1984 | Smith | 2/438 |
| 4,528,701 | 7/1985 | Smith | 2/438 |
| 4,748,697 | 6/1988 | Hodnett | 2/438 |

Primary Examiner—Clifford D. Crowder
Assistant Examiner—Jeanette E. Chapman
Attorney, Agent, or Firm—Charles C. Logan, II

[57] ABSTRACT

A disposable vision clearing device for painting or the like that is formed from three basic components: a flat die cut card stock paper housing blank, a flat die cut card stock paper interior assembly blank and a transparent sheet of film having its one end mounted on a supply roll and its other end mounted on a take-up reel. These basic components are assembled together in a predetermined manner and tab members on the respective paper blank members have adhesive applied to them and two important assembled structures are formed. They are the top and bottom tracks along which the respective top and bottom edges of the sheet of film can travel as it advances across the aligned cutout window portions. Other important assembled structures are the sealed enclosure for the supply roll and the sealed enclosure for the take-up reel. The disposable vision clearing device can worn over safety goggles or over the lens of a full face respirator in addition to being used alone by itself without either of these other devices.

6 Claims, 3 Drawing Sheets

VISION CLEARING DEVICE

BACKGROUND OF THE INVENTION

The present invention relates to protective vision devices, and particularly relates to devices which protect from potentially obstructive material such as spray paints and coatings.

There exists many industrial applications in which materials are deposited on to surfaces with spray techniques, one common example of which is spray painting. Because such spraying, and particularly spray painting techniques, often tend to fill their immediate surroundings and environment with the material being sprayed, appropriate precautions must be made to safeguard the health and safety of individual workers present the environment.

One immediate concern is the protection of a worker's eyes, particularly since many materials which are not otherwise hazardous to skin, or for which ordinary clothing provides appropriate protection, are much more hazardous to eyesight, with the potential to cause either temporary or permanent harm. A typical solution providing eye protection is some sort of eye wear, usually in the form of glasses or goggles. Where the only requirement for the glasses or goggles is to serve as a barrier to physical entry into the eye of non-toxic materials, such glasses or goggles may be somewhat satisfactory. Nevertheless, even in non-toxic painting environments goggles or glasses have one particular disadvantage: at some point paint will almost certainly coat the vision portion of the glasses or goggles to the extent that they must be cleaned—either in water or more hazardous solvents—or simply discarded.

Accordingly, for a worker to stop painting every few moments to clean away accumulated paint is time-consuming and distracting. Oftentimes paint dries too quickly for the lens to be cleaned in any fashion whatsoever without some sort of solvent. Solvents in turn can create adverse effects on the lens and obscure the visibility making them useless. Typically, such goggles tend to be inconvenient to use and are often neglected by workers in spite of laws and regulations which require such protection.

A number of attempts have been made to address the problem of clearing the field of vision of a pair of glasses or goggles when they become dirty from particular materials. One type of device provides a plurality of superimposed layers of disposable transparent material which can be successively removed as each becomes soiled. In these devices, however, only a few layers of transparent material can be superimposed, typically about five, without distorting the field of vision. This usually represents too few cleaning surfaces from a practical standpoint because some tasks, for example painting a ceiling, will require 30 or more clean changes of the field of vision. In practice, sprayed paint also tends to accumulate between the layers, aggravating the problem rather than addressing it. Other devices take the form of some sort of supply and take-up system of transparent film which extends across a wearer's field of vision to renew a clean surface as the film is advanced. These devices have generally proved unsatisfactory, however, because of the cumbersome nature of changing an exhausted supply of film.

Furthermore, as paint or other materials build up within the supply and take-up or other advancement systems, such as systems become inoperative, rendering the devices no more useful than simple goggles or safety glasses.

Additionally, workers typically wear gloves when toxic materials are in use. Accordingly, the task of renewing the transparent film in such devices, or replacing the entire supply, becomes extremely difficult and cumbersome for the user.

Accordingly, it is an object of the invention to provide a vision protecting device made of card stock paper and which is relatively inexpensive so that the entire unit is disposable once the roll of transparent film has been exhausted.

It is a further object of the invention to provide a vision protecting device which includes an advancement mechanism which conveniently advances a renewable lens surface across the field of vision of a wearer.

SUMMARY OF THE INVENTION

The present invention comprises a vision clearing device that is made from essentially three major components. Two of these components are made of flat card stock paper that is die cut to form a paper housing blank and a paper interior assembly blank. The third major component is an elongated sheet of transparent film whose one end is mounted on a supply roll and whose other end is mounted on a take-up reel.

In the assembly operation the transparent sheet of film is positioned with its opposite ends stretching over a cutout window portion in the paper housing blank. The interior assembly paper blank is then positioned on top of the sheet of transparent film so that its cutout window portion aligns with the cutout window portion of the paper housing blank. Next the paper housing blank and paper interior assembly blank are folded about their predetermined fold lines and their mating tab portions are adhesively secured to each other in a predetermined manner. In its assembled form, the supply roll and the take-up reel are each located in their own individual sealed enclosures. A finger crank extending from the bottom of one of the sealed enclosures allows the transparent sheet of film to be selectively advanced across the cutout window portion of the device. Due to the inexpensive cost of the card stock paper used for making two of the major structures of the vision clearing device, the assembled product is relatively inexpensive to manufacture and can thus be produced as a disposable vision clearing device.

The foregoing objects and advantages and features of the present invention and the manner in which the same are accomplished will be more readily apparent upon consideration of the detailed description and the following drawings in which:

DESCRIPTION OF THE PREFERRED EMBODIMENT

The novel disposable vision clearing device will now be described by referring to FIGS. 1-6 of the drawings. The device is generally designated numeral 10.

Figure 1:
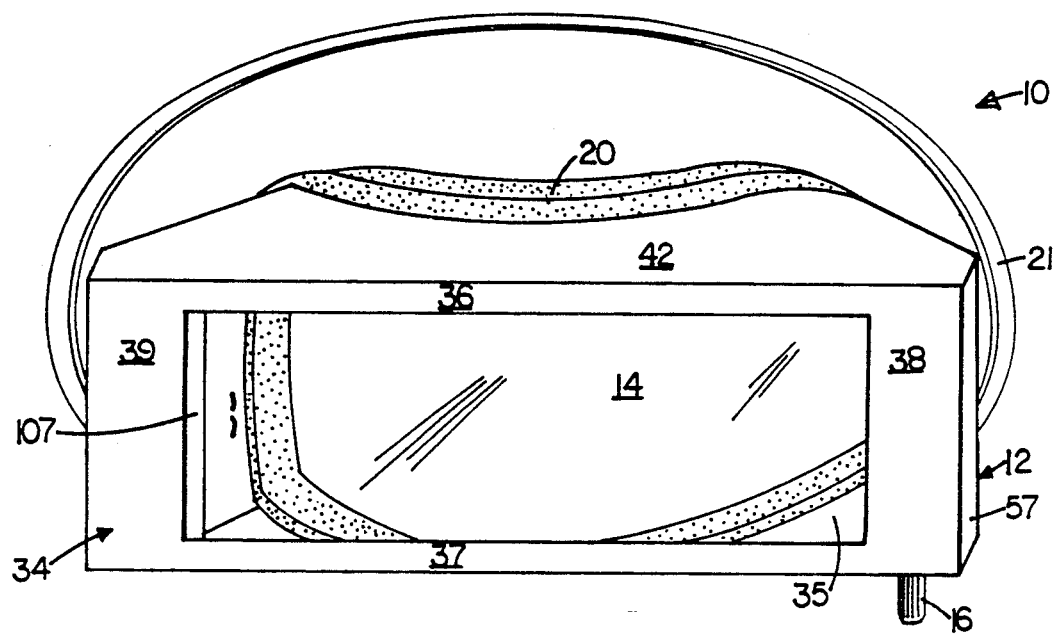
FIG. 1 is a front perspective view of the vision clearing device.

Vision clearing device 10 is illustrated in its assembled state in FIG. 1. It has a housing 12 within which is mounted a transparent sheet of film 14. A crank 16 is connected to the bottom of the take-up reel 26 and it extends from the bottom wall of the housing. A foam strip or collar 20 extends around the open rear end of housing 12 and fits against the face of the wearer. An elastic band 21 secures the vision clearing device to the wearer's head.

Figure 2:
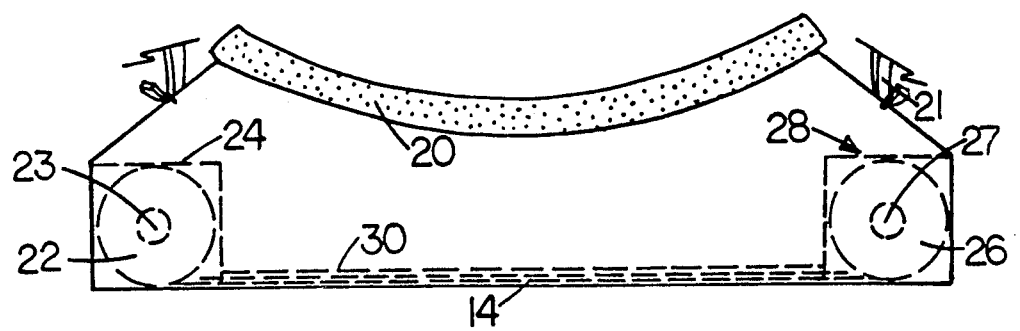
FIG. 2 is a schematic top plan view of the vision clearing device.

FIG. 2 is a schematic top plan view showing the supply roll 22 mounted on a tube 23 in sealed enclosure 24. Take-up reel 26 has a tube 27 whose bottom end is connected to crank 16. Take-up reel 26 is mounted in sealed enclosure 28. Transparent film 14 passes along a planar path between enclosure 24 and enclosure 28 in a top track and a bottom track whose structure will later be described. Lens 30 is mounted in the interior of housing 12 between the respective sealed enclosures 24 and 28 and it is slightly spaced from the sheet of film that passes across its front face.

Figure 3D:
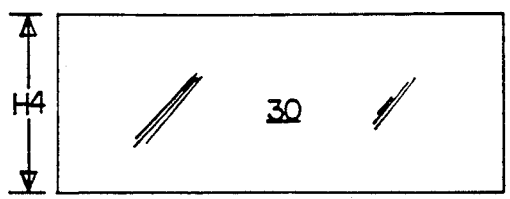
FIG. 3D is a top plan view of the lens.
Figure 3B:
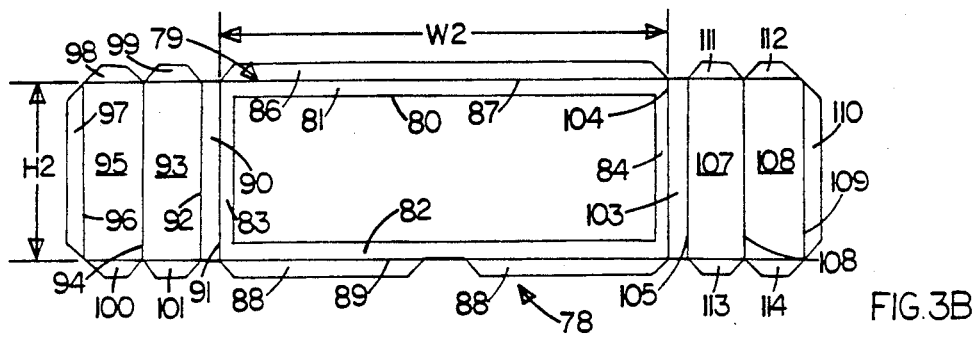
FIG. 3B is a top plan view of the flat die cut paper blank interior assembly.
Figure 3C:
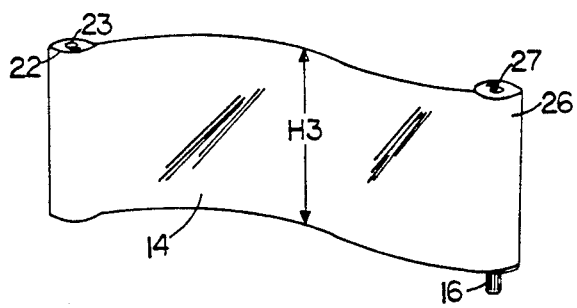
FIG. 3C is a front perspective view of the transparent sheet of film mounted on the supply roll and the take-up reel.
Figure 3A:
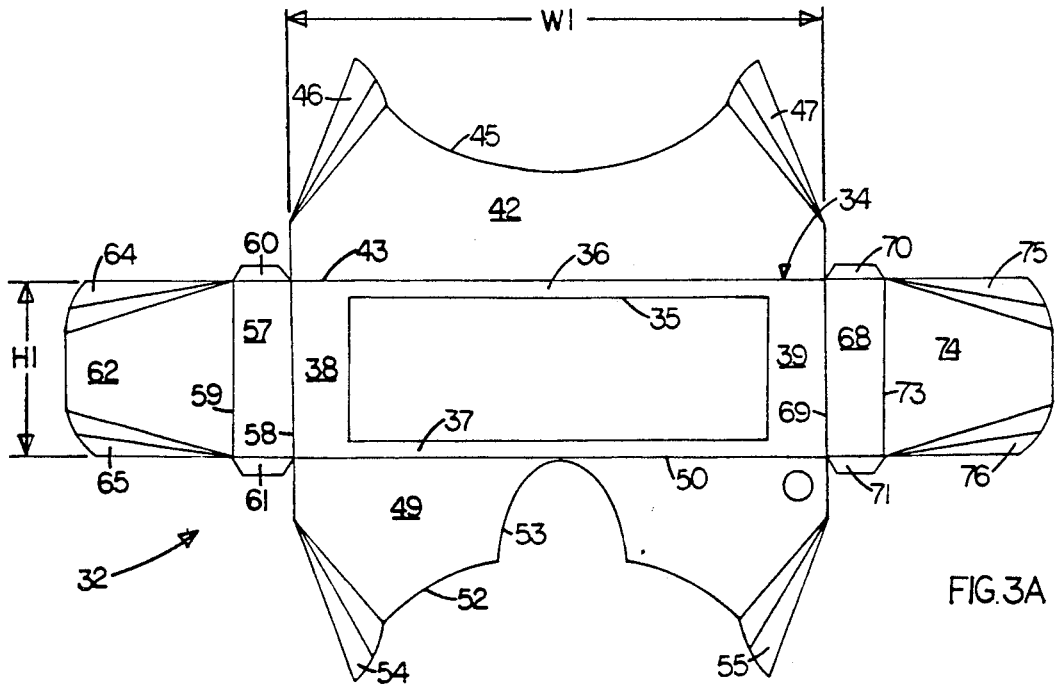
FIG. 3A is a top plan view of the flat die cut paper housing blank.

Flat die cut card stock paper housing blank 32 is illustrated in FIG. 3A. It has a planar front wall panel 34 having a predetermined height H1. A cutout window portion 35 in front wall panel 34 forms a top frame portion 36, a bottom frame portion 37, a left side frame portion 38 and a right side frame portion 39. Top wall 42 is connected along fold line 43 to front wall panel 34. It has a curved forehead edge 45 and overlapping flap portions 46 and 47. Bottom wall 49 has a fold line 50 connecting it to front wall panel 34. It has a curved sheet edge 52 and a nose cutaway portion 53. Overlapping flap portions 54 and 55 are formed adjacent the opposite ends of bottom wall 49 and they each have predetermined fold lines. Front wall panel 34 has a width W1.

A left side primary wall portion 57 has fold lines 58 and 59 and tabs 60 and 61. A trapezoidal shaped secondary left side wall portion 62 has one of its edges on fold line 59 and it has overlapping flap portions 64 and 65 each of which have their own fold lines.

Right side primary wall portion 68 is connected to front wall panel 34 by fold line 69. It has tabs 70 and 71 and a fold line 73 that connects it to trapezoidal shaped right side wall portion 74. Overlapping flap portions 75 and 76 have their own respective fold lines.

The flat die cut card stock paper interior assembly blank 78 is best illustrated in FIG. 3B. It has a rear wall panel 79 having a predetermined height H2 and a predetermined width W2. Cutout window portion 80 forms a top frame section 81, a bottom frame section 82, a left side frame section 83 and a right side frame section 84. A top edge tab member 86 extends from fold line 87. A pair of bottom edge tab members 88 extend from fold line 89. A spacer member 90 extends from fold line 91 and it has another fold line 92 that is connected to right side wall portion 93. A fold line 94 is connected to rear wall portion 95 and a tab 97 extends from fold line 96. Tabs 98-101 extend from the respective wall portions 93 and 95. A spacer 104 extends from fold line 103 and it also has a fold line 105 that connects it to rear wall portion 107. Fold line 108 connects it to rear wall portion 108 that in turn has fold line 109 connecting to a tab 110. Tabs 111-114 extend from the respective right side wall portion and rear wall portions 107 and 108.

FIG. 3C shows the transparent sheet of film 14 and it has a predetermined height H3 that is never greater than H2. Lens 30 is illustrated in FIG. 3D and it has a height H4 that is never greater than H1.

In the assembly process, transparent sheet of film 14 is positioned on the rear surface of front wall panel 34. The rear wall panel 79 of interior assembly blank 78 is then placed over film 14. Top edge tab member 86 is secured by adhesive to top wall 42 adjacent fold line 43 and the space between the respective top frame sections 36 and 81 form a top track for guiding the top edge of film sheet 14. Tabs 88 of rear wall panel 79 are secured by adhesive to bottom wall 49 adjacent fold line 50 and the space between them forms a track for the bottom edge of the transparent film 14.

The sealed enclosure for the supply reel 22 is formed by left side frame portion 38, left side primary wall portion 57, right side wall portion 93 and rear wall portion 95. The tabs at the respective top and bottom edges of these members have adhesive applied to them so that they can be secured to top wall 42 and bottom wall 49. Overlapping flap portions 46 and 64 are secured to each other by adhesive in the same manner that overlapping flap portions 54 and 65 are secured to each other.

The sealed enclosure for take-up reel 26 is formed by right side frame portion 39, right side primary wall portion 68, right side wall portion 107, and rear wall portion 108. The respective top and bottom tabs for these members are secured to the respective top wall 42 and bottom wall 49 by adhesive. Overlapping flap portions 47 are secured by adhesive to overlapping flap portions 75. Overlapping flap portions 55 are secured by adhesive to overlapping flap portions 76.

Figure 5:
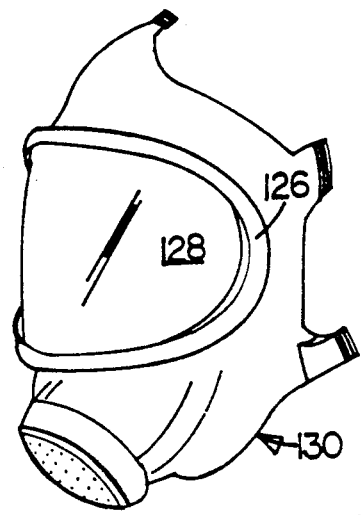
FIG. 5 is a front perspective view of a typical full-face respirator to which the vision clearing device illustrated in FIG. 4 can be attached by its clip member.
Figure 4:
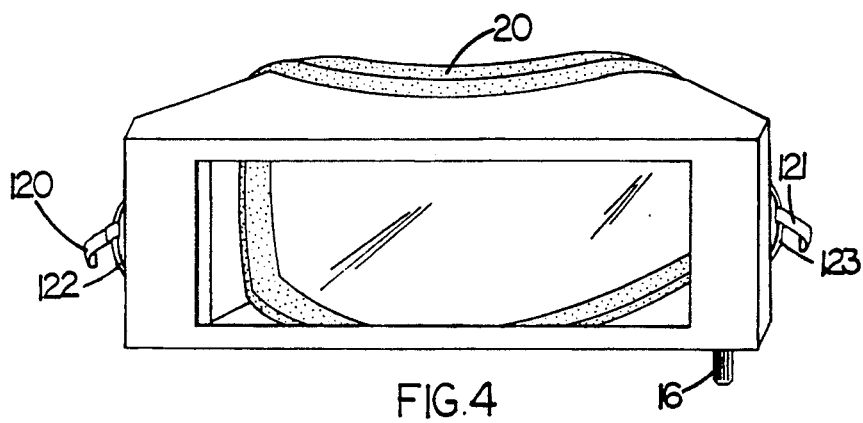
FIG. 4 is a front perspective view illustrating attachment clips secured to its opposite lateral sides.

Referring to FIGS. 4 and 5, vision clearing device 10 may have clips 120 and 121 attached to it by the respective closed loop straps 122 and 123. These clips 120 and 121 are attachable to the ring 126 and its flange that surrounds lens 128 of a typical full-faced respirator 130.

Figure 6:
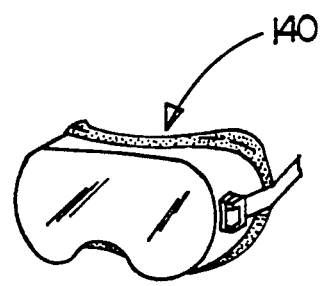
FIG. 6 is a front perspective view of a typical safety goggle which can be worn by an individual underneath the vision clearing device illustrated in FIG. 1.

The safety goggles 140 illustrated in FIG. 6 are small enough in height and width so that they can be worn under vision clearing device 10.

What is claimed is:

1. A disposable vision clearing device for painting or the like comprising:
    a card stock paper housing having a planar front wall panel with a cutout window portion that defines a top frame portion, a bottom frame portion, a left side frame portion and a right side frame portion, said front wall panel having a predetermined width (W1), a predetermined height (H1), a front surface and a rear surface;
    said front wall panel having a top edge that defines a fold line that is connected to a top wall;
    said front wall panel having a bottom edge that defines a fold line that is connected to a bottom wall;

said front wall panel having a left edge that defines a first fold line that is connected to a left side primary wall portion;

said front wall having a right edge that defines a first fold line that is connected to a right side primary wall portion;

a card stock paper interior assembly having a planar rear wall panel with a cutout portion that defines a top frame section, a bottom frame section, a left side frame section, and a right side frame section, said rear wall panel having a predetermined width (W2) a predetermined height (H2), a front surface and a rear surface;

said rear wall panel having a top edge that defines a fold line that is connected to a top edge tab member;

said rear wall panel having a bottom edge that defines a fold line that is connected to a bottom edge tab member;

an elongated transparent sheet of film having its one end mounted on a supply roll and its other end mounted on a take-up reel, said sheet having a predetermined height H3;

said sheet of film being stretched across the rear surface of said front wall panel and its cutout window portion with said supply roll positioned adjacent said left side frame portion and said take-up reel positioned adjacent said right side frame portion;

said rear wall panel having its front surface positioned on said sheet of film so that its cutout window portion aligns with the cutout window portion of said front wall panel;

means securing the top edge tab member of said rear wall panel to the rear surface of the top wall of said front wall panel to form a top track between said front and rear wall panels along which the top edge of said sheet of film can travel as it advances across said aligned cutout window portions;

means securing the bottom edge tab member of said rear wall panel to the rear surface of the bottom wall of said front wall panel to form a bottom track between said front and rear wall panels along which the bottom edge of said sheet of film can travel as it advances across said aligned said cutout window portion;

said rear wall panel having a left edge that defines a first fold line that is connected to means for forming the right side wall portion and rear wall portion of a sealed enclosure for said supply roll, the other two side walls of said enclosure being the left side primary wall portion and the left side frame portion of said front wall panel; and said rear wall panel having a right edge that defines a first fold line that is connected to means for forming the left side wall portion and rear wall portion of a sealed enclosure for said take-up reel, the other two side walls of said enclosure being the right side primary wall portion and the right side frame portion of said front wall panel.

2. A disposable vision clearing device as recited in claim 1 further comprising external means for advancing said film on said take-up reel.

3. A disposable vision clearing device as recited in claim 1 further comprising a lens positioned adjacent the rear surface of said rear wall panel and it essentially extends between said supply roll sealed enclosure and said take-up reel sealed enclosure.

4. A disposable vision clearing device as recited in claim 1 further comprising an elastic strap attached to said front wall panel for holding said device on a person's head.

5. A disposable vision clearing device as recited in claim 1 further comprising means for detachably securing said vision clearing device over the lens of a full face respirator.

6. A disposable vision clearing device as recited in claim 1 wherein said card stock paper housing and stock paper interior assembly are both formed from flat sheets of material each having predetermined fold lines that allow them to be folded into their assembled shape.

* * * * *